United States Patent
Box et al.

(10) Patent No.: US 7,317,040 B2
(45) Date of Patent: Jan. 8, 2008

(54) NITRIC OXIDE SYNTHASE INHIBITOR PHOSPHATE SALT

(75) Inventors: David Box, Stevenage (GB); David Colclough, Dartford (GB); Iain Gillies, Waterlooville (GB); Michael Simon Loft, Dartford (GB); Rebecca Moore, Dartford (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 161 days.

(21) Appl. No.: 10/451,299

(22) PCT Filed: Dec. 17, 2001

(86) PCT No.: PCT/GB01/05596

§ 371 (c)(1),
(2), (4) Date: Nov. 11, 2003

(87) PCT Pub. No.: WO02/50021

PCT Pub. Date: Jun. 27, 2002

(65) Prior Publication Data

US 2004/0087654 A1  May 6, 2004

(30) Foreign Application Priority Data

Dec. 21, 2000 (GB) .................. 0031179.5

(51) Int. Cl.
*A61K 31/195* (2006.01)
*A61K 31/155* (2006.01)
*C07C 257/00* (2006.01)
*A01N 37/12* (2006.01)
*A01N 37/52* (2006.01)

(52) U.S. Cl. ............... 514/562; 514/631; 560/148; 562/556; 564/225

(58) Field of Classification Search ............... 562/556, 562/533; 514/562
See application file for complete search history.

(56) References Cited

U.S. PATENT DOCUMENTS 5,889,056 A  3/1999  Hodson et al.
6,156,341 A  12/2000  Backensfeld et al.

FOREIGN PATENT DOCUMENTS

WO   WO 98 30537   7/1998
WO      9946240 A2   9/1999
WO   WO 99 59566  11/1999

OTHER PUBLICATIONS

Bastin, et al. Salt selection and optimisation procedures for pharmaceutical new chemical entities. Organic Process & Development 2000, 4, 427-435.*
Wikipedia Phosphoric acid Feb. 15, 2006.*
Riedermann et al. Expert Opin. Biol. Ther. 2003, 3(2), 339-350.*
Young et al.; "Inhibition of Inducible Nitric Oxide Synthase by Acetamidine Derivatives of Hetero-Substituted Lysine and Homolysine"; Bioorg. Med. Chem. Lett.; 2000; vol. 10(6); pp. 597-600.

* cited by examiner

*Primary Examiner*—Johann Richter
*Assistant Examiner*—Ernst V Arnold
(74) *Attorney, Agent, or Firm*—Bonnie L. Deppenbrock

(57) ABSTRACT

A compound of formula (I):

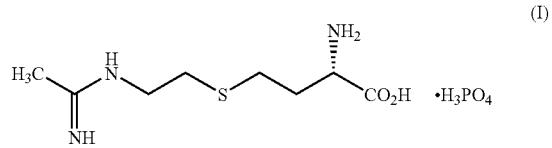

namely (2S)-2-amino-4-{[2-(ethanimidoylamino)ethyl]thio}butanoic acid, compound with phosphoric acid, or a solvate or physiologically functional derivative thereof, is useful as a relatively non-hygroscopic selective inhibitor of inducible nitric oxide synthase.

9 Claims, 7 Drawing Sheets

NITRIC OXIDE SYNTHASE INHIBITOR PHOSPHATE SALT

CROSS REFERENCES TO RELATED APPLICATIONS

This application is a 371 Application of PCT/GB01/05596, filed 17 Dec. 2001, which claims priority to GB Application Ser. No. 0031179.5, filed 21 Dec. 2000.

BACKGROUND OF THE INVENTION

The present invention relates to novel amidino compounds, to a process for their manufacture, to pharmaceutical compositions containing them, and to their use in therapy, in particular their use as selective inhibitors of inducible nitric oxide synthase.

Nitric oxide is the endogenous stimulator of the soluble guanylate cyclase enzyme and is involved in a number of biological actions. Excess nitric oxide production is also thought to be involved in a number of conditions, including septic shock and many inflammatory diseases. The biochemical synthesis of nitric oxide from L-arginine is catalysed by the enzyme NO synthase. Many inhibitors of NO synthase have been described and proposed for therapeutic use.

More recently, it has been an object in this field to provide NO synthase inhibitors displaying selectivity for either inducible NO synthase (iNOS) or neuronal NO synthase (nNOS) over endothelial NO synthase (eNOS).

Thus WO98/30537 describes selective NO synthase inhibitors of formula

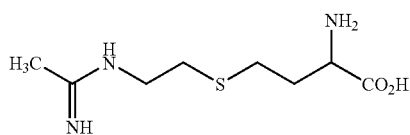

or a salt, solvate, or physiologically functional derivative thereof.

Suitable salts according to WO98/30537 include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, succinic, oxalic, fumaric, maleic, oxaloacetic, methanesulphonic, ethanesulphonic, p-toluenesulphonic, benzenesulphonic, and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine. Hydrochloride salts are exemplified and are stated to be hygroscopic.

DETAILED DESCRIPTION OF THE INVENTION

The present invention seeks to provide a selective iNOS inhibitor which is considerably less hygroscopic than, for example, the hydrochloride salts exemplified in WO98/30537.

We have now found compounds falling within the scope of WO98/30537 which are selective iNOS inhibitors and display advantages, including being relatively non-hygroscopic. A compound which is relatively non-hygroscopic is useful because it does not readily absorb moisture from the atmosphere and is therefore easier to isolate, formulate and handle.

According to the present invention there is provided a compound of formula (I)

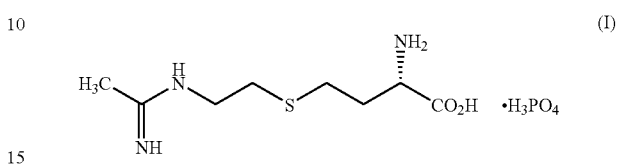

or a solvate or physiologically functional derivative thereof.

The present invention therefore provides (2S)-2-amino-4-{[2-(ethanimidoylamino)ethyl]thio}butanoic acid, compound with phosphoric acid, or a solvate (preferably hydrates) or physiologically functional derivative thereof. The present invention includes all polymorphs of this compound. Preferably each molecule of the compound of formula (I) is associated with at least one molecule of water, such as 1, 2 or 3 water molecules, especially 1 or 3 water molecules. In a particularly preferred aspect, the present invention provides (2S)-2-amino-4-{[2-(ethanimidoylamino)ethyl]thio}butanoic acid, compound with phosphoric acid, (1:1) hydrate.

It will be appreciated by those skilled in the art that phosphoric acid exists in more than one form. The preferred form for use in the context of the present invention is orthophosphoric acid.

Preferably, the compound of formula (I) does not substantially deliquesce (ie rapidly take up atmospheric moisture) below a relative humidity of 60% at 25 degrees C. More preferably, the compound of formula (I) does not substantially deliquesce below a relative humidity of 70% at 25 degrees C.

Preferably, the compound of formula (I) does not undergo a mass change via adsorption of more than 5% w/w at a relative humidity of 70% at 25 degrees C. More preferably, the compound of formula (I) does not undergo a mass change via adsorption of more than 2% w/w at a relative humidity of 70% at 25 degrees C. Most preferably, the compound of formula (I) does not undergo a mass change via adsorption of more than 1% w/w at a relative humidity of 70% at 25 degrees C.

Solvates of the compound of formula (I) which are suitable for use in medicine are those wherein the associated solvent is pharmaceutically acceptable. However, solvates having non-pharmaceutically acceptable associated solvents are within the scope of the present invention, for example, for use as intermediates in the preparation of the compound of formula (I) and its solvates, and physiologically functional derivatives.

By the term "physiologically functional derivative" is meant a chemical derivative of the compound of formula (I) having the same physiological function as the compound of formula (I), for example, by being convertible in the body thereto. According to the present invention, examples of physiologically functional derivatives include esters, amides, and carbamates; preferably esters and amides.

Pharmaceutically acceptable esters and amides of the compound of formula (I) may have the acid group converted to a $C_{1-6}$ alkyl, aryl, aryl $C_{1-6}$ alkyl, or amino acid ester or amide. Pharmaceutically acceptable amides and carbamates of the compound of formula (I) may have an amino group converted to a $C_{1-6}$ alkyl, aryl, aryl $C_{1-6}$ alkyl, or amino acid amide or carbamate.

As mentioned above, the compound of formula (I) is an inhibitor of NO synthase. WO98/30537 demonstrates this generally for compounds of the following formula

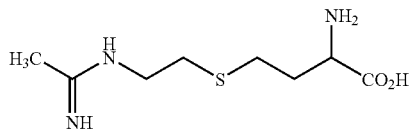

or a salt, solvate, or physiologically functional derivative thereof: phosphate salts are not exemplified.

The compound of formula (I) and its pharmaceutically acceptable solvates and physiologically functional derivatives have use in the prophylaxis and treatment of clinical conditions for which an inhibitor of NO synthase is indicated, in particular an inhibitor of iNOS. Such conditions include inflammatory conditions, shock states, immune disorders, and disorders of gastrointestinal motility. The compound of formula (I) and its pharmaceutically acceptable solvates, and physiologically functional derivatives thereof may also be of use in the prophylaxis and treatment of diseases of the central nervous system including migraine and metabolic disorders including dyslipidemia.

By shock states is meant those resulting from overproduction of NO, such as septic shock, haemorrhagic shock, traumatic shock, or shock caused by fulminant hepatic failure or by therapy with cytokines such as TNF, IL-1 and IL-2 or therapy with cytokine-inducing agents, for example 5,6-dimethylxanthenone acetic acid.

Examples of inflammatory conditions and immune disorders include those of the joint, particularly arthritis (e.g. rheumatoid arthritis, osteoarthritis, prosthetic joint failure), or the gastrointestinal tract (e.g. ulcerative colitis, Crohn's disease, and other inflammatory bowel diseases, gastritis and mucosal inflammation resulting from infection, the enteropathy provoked by non-steroidal anti-inflammatory drugs), of the airways (e.g. adult respiratory distress syndrome, asthma, cystic fibrosis, upper respiratory tract inflammatory disease (e.g. rhinitis such as allergic rhinitis) or chronic obstructive pulmonary disease), of the heart (e.g. myocarditis), of nervous tissue (e.g. multiple sclerosis), of the pancreas (e.g. diabetes melitus and complications thereof), of the kidney (e.g. glomerulonephritis), of the skin (e.g. dermatitis, psoriasis, eczema, urticaria), of the eye (e.g. glaucoma) as well as of transplanted organs (e.g. rejection) and multi-organ diseases (e.g. systemic lupus erythematosis) and inflammatory sequelae of viral or bacterial infections.

Furthermore, there is evidence for overproduction of NO by iNOS in atherosclerosis and following hypoxic or ischaemic insults (with or without reperfusion), for example in the brain or in ischaemic heart disease.

Disorders of gastrointestinal motility include ileus, for example post-operative ileus and ileus during sepsis.

By diseases of the central nervous system is meant those for which overproduction of NO is implicated, for example migraine, psychosis, anxiety, schizophrenia, sleep disorders, cerebral ischaemia, CNS trauma, epilepsy, multiple sclerosis, AIDS dementia, chronic neurodegenerative disease (e.g. Lewy Body Dementia, Huntington's disease, Parkinson's disease, or Alzheimer's disease) and acute and chronic pain, and conditions in which non-adrenergic non-cholinergic nerve may be implicated such as priapism, obesity and hyperphagia.

Examples of acute pain include musculoskeletal pain, post operative pain and surgical pain. Examples of chronic pain include chronic inflammatory pain (e.g. rheumatoid arthritis and osteoarthritis), neuropathic pain (e.g. post herpetic neuralgia, diabetic neuropathies associated with diabetes, trigeminal neuralgia, pain associated with functional bowel disorders, e.g. irritable bowel syndrome, non cardiac chest pain and sympathetically maintained pain) and pain associated with cancer and fibromyalgia.

Overproduction of NO is implicated in metabolic disorders through its effect on lipoprotein lipase activity causing hypertriglyceridemia. Selective inhibitors of iNOS will be useful in metabolic conditions where NO over-production is implicated, such as dyslipidaemia.

Furthermore, inhibition of NO synthase may be of advantage in preventing the lymphocyte loss associated with HIV infection, in increasing the radiosensitivity of tumours during radiotherapy and in reducing tumour growth, tumour progression, angiogenesis, and metastasis.

Accordingly, the present invention provides a method for the prophylaxis or treatment of a clinical condition in a mammal, such as a human, for which an inhibitor of nitric oxide synthase, for example, an iNOS inhibitor is indicated, which comprises administration of a therapeutically effective amount of a compound of formula (I), or a pharmaceutically acceptable solvate or physiologically functional derivative thereof. In particular, the present invention provides a method for the prophylaxis or treatment of an inflammatory and/or immune disorder, such as arthritis, allergic rhinitis or asthma. In a further preferred aspect the present invention provides a method for the prophylaxis or treatment of a clinical condition selected from pain, migraine, ileus and irritable bowel syndrome.

In the alternative, there is also provided a compound of formula (I) or a pharmaceutically acceptable solvate or physiologically functional derivative thereof for use in medical therapy, particularly for use in the prophylaxis or treatment of a clinical condition in a mammal, such as a human, for which an inhibitor of nitric oxide synthase, for example an iNOS inhibitor, is indicated. In particular, there is provided a compound of formula (I) or a pharmaceutically acceptable solvate or physiologically functional derivative thereof for the prophylaxis or treatment of an inflammatory and/or immune disorder, such as arthritis, allergic rhinitis or asthma. In a further preferred aspect, there is provided a compound of formula (I) or a pharmaceutically acceptable solvate or physiologically functional derivative thereof for the prophylaxis or treatment of pain, migraine, ileus or irritable bowel syndrome.

The amount of the compound of formula (I), or a pharmaceutically acceptable solvate or physiologically functional derivative thereof which is required to achieve a therapeutic effect will, of course, vary with the particular compound, the route of administration, the subject under treatment, and the particular disorder or disease being treated. The compounds of the invention may be administered orally or via injection at a dose of from 0.001 to 200 mg/kg per day, preferably 0.01 to 20 mg/kg per day. The dose range for adult humans is generally from 0.1 mg to 10 g/day and preferably 1 mg to 1 g/day. Tablets or other forms of presentation provided in discrete units may conveniently contain an amount of compound of the invention which is effective at such dosage or as a multiple of the same, for instance, units containing 0.1 mg to 500 mg, usually around 1 mg to 200 mg.

While it is possible for the compound of formula (I), or a pharmaceutically acceptable solvate or physiologically functional derivative thereof to be administered alone, it is preferable to present them as a pharmaceutical formulation.

Accordingly, the present invention further provides a pharmaceutical formulation comprising a compound of formula (I) or a pharmaceutically acceptable solvate or physiologically functional derivative thereof, and a pharmaceutically acceptable carrier or excipient, and optionally one or more other therapeutic ingredients.

The present invention also provides the use of a compound of formula (I), or a pharmaceutically acceptable solvate or physiologically functional derivative thereof in the manufacture of a medicament for the prophylaxis or treatment of a clinical condition for which an inhibitor of nitric oxide synthase, for example an iNOS inhibitor, is indicated, for example an inflammatory and/or immune disorder, such as arthritis, allergic rhinitis or asthma. In a further preferred aspect, there is provided a compound of formula (I), or a pharmaceutically acceptable solvate or physiologically functional derivative thereof in the manufacture of a medicament for the prophylaxis or treatment of a clinical condition selected from pain, migraine, ileus and irritable bowel syndrome.

Hereinafter, the term "active ingredient" means a compound of formula (I), or a pharmaceutically acceptable solvate or physiologically functional derivative thereof.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The relatively non-hygroscopic nature of the compound of formula (I) renders it particularly suitable for administration in solid form e.g. as tablets.

In a preferred aspect the present invention provides a solid dosage form comprising the compound of formula (I) or a solvate or physiologically functional derivative thereof.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

According to a further aspect of the invention, there is provided a process for preparing a compound of formula (I) or a solvate or physiologically functional derivative thereof which comprises:

(i) reacting a compound of formula (II)

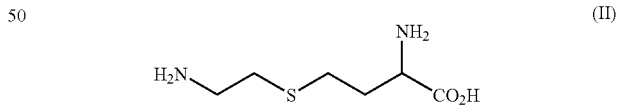

or an enantiomer, a salt, or a protected derivative thereof, with a compound of formula (III)

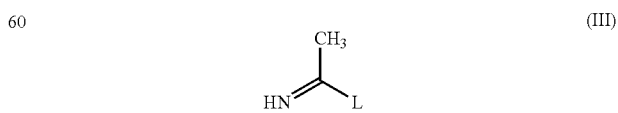

or a salt thereof, wherein L is a leaving group, most suitably a $C_{1-6}$ alkoxy group (for example ethoxy), an alkylthio group, an aralkylthio group, an arylthio group (for example benzylthio), a 1- or 2-naphthylmethylthio group or a heterocycle group; followed by the following steps in any order:

(ii) converting the resulting compound to the monophosphate salt;

(iii) optional removal of any protecting groups;

(iv) optional separation of an enantiomer from a mixture of enantiomers;

(v) optional conversion of the product to a corresponding solvate or physiologically functional derivative thereof.

Preferably compounds of formula (I) prepared by this method are purified by recrystallization from a suitable solvent, such as an aqueous solvent, for example, water, an aqueous alcohol or aqueous acetonitrile, or a polar organic solvent, for example N,N-dimethylformamide, dimethylsulphoxide, dimethylacetamide or 1-methyl-2-pyrrolidinone. A preferred solvent for recrystallization is aqueous ethanol.

In a preferred embodiment, the compound that results from the reaction of the compounds of formulae (II) and (III) is reacted with phosphoric acid, preferably orthophosphoric acid, to form the compound of formula (I).

Preferably, the step of converting the resulting compound to the phosphate salt comprises a biphasic reaction using toluene and aqueous phosphoric acid.

In a preferred embodiment, following step (i): toluene is added to an aqueous layer resulting from the reaction of the compound of formula (II) or an enantiomer, a salt, or a protected derivative thereof with the compound of formula (III) or a salt thereof to form a biphasic mixture; a toluene layer is separated from this mixture; an aqueous solution of phosphoric acid is added to the toluene layer to form a further biphasic mixture; and an aqueous layer is separated from this further mixture.

When L is $C_{1-6}$ alkoxy, the reaction in step (i) above may be effected in solution at alkaline pH, for example pH 8 to 11, suitably at pH p. 5 to 10.5, and at a low temperature, for example −5° C. to 25° C. When L is an alkylthio, aralkylthio, or arylthio group, the reaction may be effected in an organic solvent e.g. dimethylformamide, tetrahydrofuran, ethyl acetate or a $C_{1-4}$ alcohol such as ethanol, at a moderate temperature e.g. 10 to 40° C., suitably at ambient temperature.

Preferably, the compound of formula (II) is

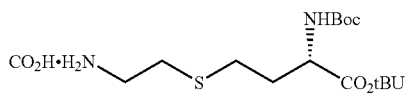

Preferably, the compound of formula (III) is

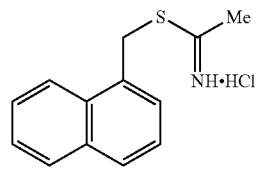

The compounds of formula (II) and derivatives thereof may be prepared by reacting a compound of formula (IV)

wherein X is a leaving group, most suitably a halo group such as Br, or an enatiomer, salt or protected derivative thereof, with the compound of formula (V).

or a salt or protected derivative thereof.

Compounds of formula (III) and salts thereof may be prepared by methods of organic chemistry well known to the person skilled in the art, for example, as described by Shearer et al in Tetrahedron Letters, 1997, 38, 179-182.

The protecting groups used in the preparation of compounds of formula (I) may be used in a conventional manner, for example, using methods described in "Protective Groups in Organic Synthesis" by Theodora W Green, 2nd edition (John Wiley and Sons, 1991) which also describes methods for the removal of such groups.

In the above reactions, primary amines are suitably protected as carbamates, such as t-butoxycarbonyl or benzyloxycarbonyl groups which may be removed under acidic conditions, for example, by treatment with hydrochloric acid or hydrobromic acid, or by hydrogenolysis.

As will be appreciated by the person skilled in the art use of such protecting groups may include orthogonal protection of amino groups in the compounds of formula (II) to facilitate the selective removal of one group in the presence of another, thus enabling selective functionalisation of a single amino function. For example, a benzyloxycarbonyl group may be selectively removed by hydrogenolysis. A person skilled in the art will also appreciate other orthogonal protection strategies, available by conventional means as described in Theodora W Green (vide supra).

The enantiomeric compounds of the invention may be obtained (a) by separation of the components of the corresponding racemic mixture, for example, by means of a chiral chromatography column, enzymatic resolution methods or preparing and separating suitable diastereoisomers, or (b) by direct synthesis from the appropriate chiral starting materials by the methods described above.

Optional conversion of a compound of formula (I) to a corresponding solvate or physiologically functional derivative may be effected by methods known to those skilled in the art. For example, the trihydrate of the compound of formula (I) may be prepared from the corresponding monohydrate via exposure to a high humidity environment for 24 hours.

BRIEF DESCRIPTION OF THE DRAWINGS

The present invention will now be described by way of example only with reference to the accompanying diagrammatic drawings in which.

EXAMPLE 1

Preparation of Compound of Formula (II)

Figure 1:
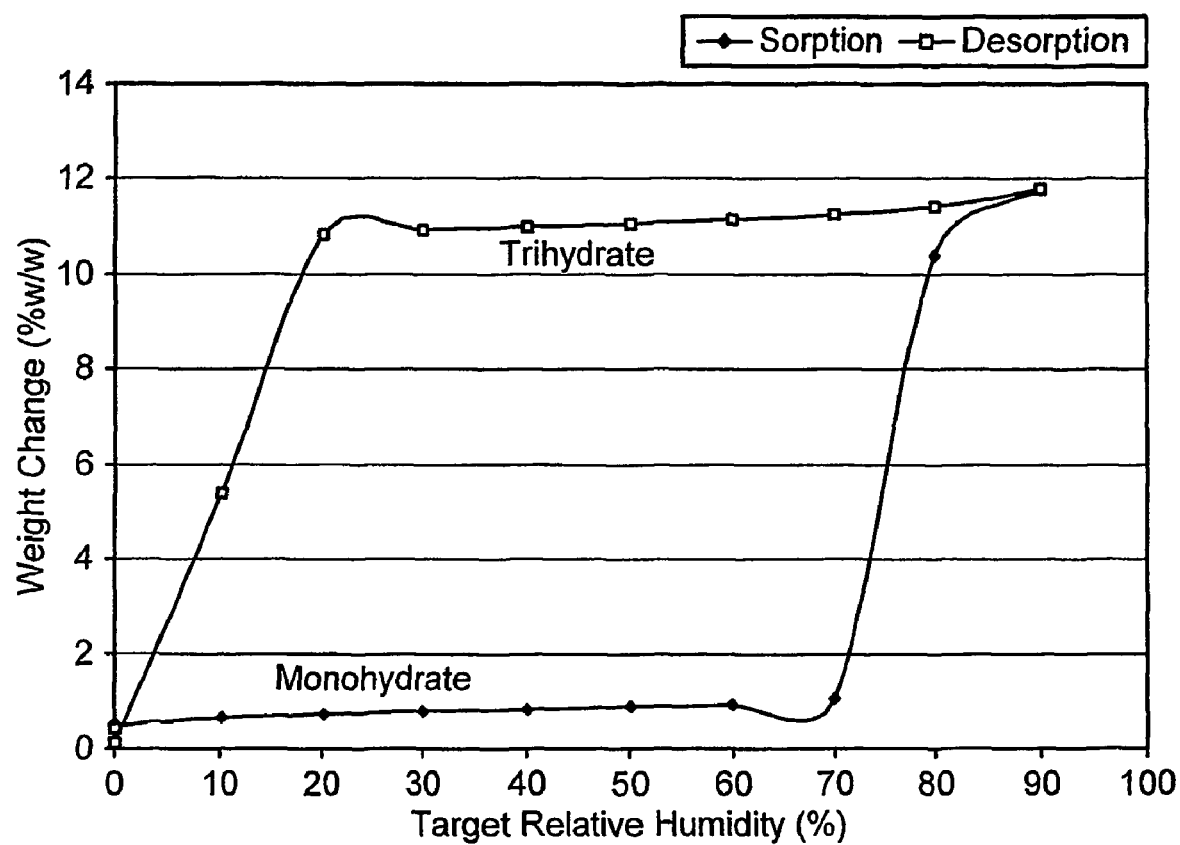
FIG. 1 is a full isotherm plot at 25 degrees C. of % target relative humidity against % weight change (w/w) showing moisture sorption and desorption for a compound of formula (I), monohydrate.

A) Stage 1: Preparation of L-Homoserine Lactone

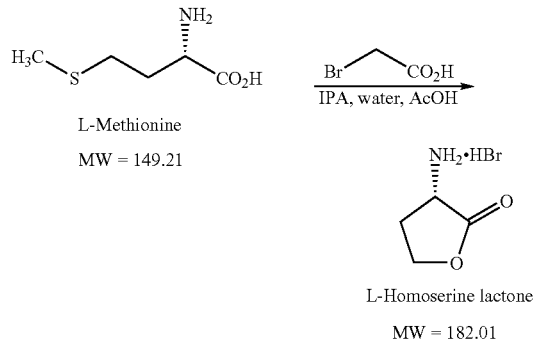

L-Methionine
MW = 149.21

L-Homoserine lactone
MW = 182.01

The reaction was carried out under a nitrogen atmosphere. A stirred suspension of L-methionine (1 mol eq., 1.0 wt) at room temperature in water (4 Vol), isopropyl alcohol (4 vol) and glacial acetic acid (1.6 vol) was prepared, to which was added bromoacetic acid (1.0 wt). The suspension was heated to 50° C. and held at that temperature for 2 hours. The temperature was raised to ca. 82-85° C. and the solution heated for a further 5 hours. The orange-brown solution was cooled and the solvents removed under reduced pressure. The thick, dark brown slurry was heated (water bath temperature 90° C.) for two hours whilst under vacuum. The slurry was allowed to cool then suspended in 4M HCl in dioxane (2 Vol) and stirred at room temperature for a minimum period of 3 hours. The crystalline solids were collected by filtration and suspended in isopropyl alcohol (1.5 vol): the suspension was stirred for at least 1 hour. The solids were collected again by filtration and dried in vacuo at 50-60° C. to give L-homoserine lactone as an off-white crystalline solid.

B) Stage 2: Preparation of (2S)-2-amino-4-bromobutanoic Acid Hydrobromide

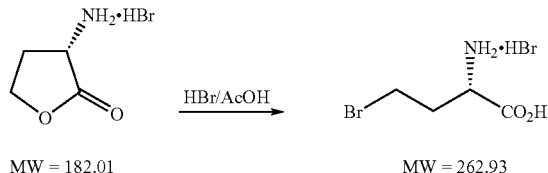

MW = 182.01

MW = 262.93

The reaction was carried out under a nitrogen atmosphere. L-Homoserine lactone (1.0 mol eq., 1.0 wt) was suspended and stirred in glacial acetic acid (2 Vol) at 20±5° C. under a static atmosphere of $N_2$. To the suspension was added (8 Vol) of a 45% w/v solution of hydrogen bromide in acetic acid. The contents were ramp heated to 52±1° C. over 4 hours, and then stirred at 52±1° C. for 16 hours to give a white solid suspended in a yellow or orange solution. The contents were cooled to 20±2° C. and held at 20±2° C. for at least two hours to allow the product to fully precipitate. The solid was collected by filtration. The cake was then washed, firstly with acetic acid (3×2 Vol) and then tert-butylmethyl ether (TBME; 3×2 vol). The product was dried to constant weight in a vacuum oven at 45±5° C. and collected as a white/off-white crystalline solid.

C) Stage 3: Preparation of tert-butyl (2S)-2-amino-4-bromobutanoate sulfate

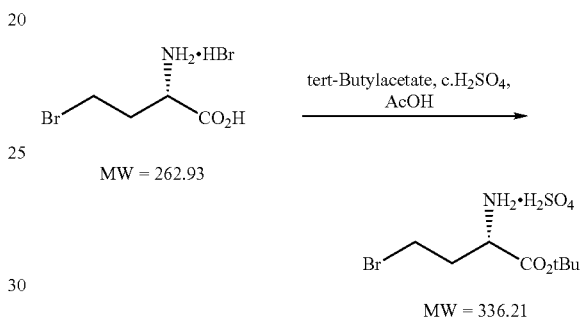

MW = 262.93

MW = 336.21

The reaction was carried out under a nitrogen atmosphere. (2S)-2-amino-4-bromobutanoic acid hydrobromide (1 mol eq., 1.0 wt) was suspended and stirred in tert-butyl acetate (10 vol.) at 5±3° C. for ca. 1 hour under an atmosphere of $N_2$. To the suspension was added, dropwise over ca. 30 minutes, concentrated sulphuric acid (1.2 eq, 0.445 wt), maintaining a contents temperature of 5±3° C. The contents were warmed to 18±3° C. and stirred at that temperature for 10 mins. Glacial acetic acid (2.5 vol) was added over ca. 10 minutes and then the reaction mixture was stirred vigorously until a clear solution was obtained (up to 3 hours). Stirring continued at 18±3° C. for at least 2 hours. Following the onset of crystallisation, the reaction mixture was aged for at least 4 hours at 18±30° C. Toluene (5.5 vol) was then added over 50 min. to the slurry. The resulting white mixture was stirred for 18 hours at 18±3° C. before collecting the product by filtration. The filter cake was washed with ethyl acetate (2.5 vol). The damp product was slurried with fresh ethyl acetate (10 vol) at 20±3° C. for 1 hour. The product was again collected by filtration and the filter cake was washed with ethyl acetate (2×2.5 vol). The product was dried in a vacuum oven at 20±5° C.

D) Stage 4: Preparation of tert-butyl (2S)-4-bromo-2-[(tert-butoxycarbonyl)amino]butanoate

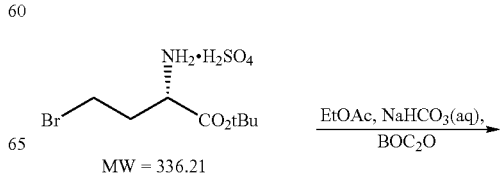

MW = 336.21

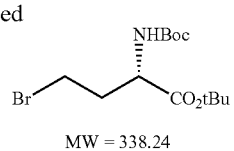

MW = 338.24

The reaction was carried out under a nitrogen atmosphere. Anhydrous sodium hydrogen carbonate (2.0 mol eq.) was vigorously stirred in water (3.0 vol) at 20±3° C. under a static $N_2$ atmosphere. Ethyl acetate (3.0 vol) was added and the mixture was cooled to 5±2° C. A solution of tert-butyl (2S)-2-amino-4-bromobutanoate sulfate (1.0 mol eq., 1.0 wt) in water (2.0 vol) was added over ca. 20 minutes, maintaining a contents temperature of 5±2° C. A solution of di-t-butyidicarbonate (0.96 eq) in ethyl acetate (2.0 vol) was then added over 5 minutes to the reaction mixture, maintaining the contents at 5±2° C. The biphasic mixture was allowed to warm to 20±3° C. and then stirred for a further 3-5 hours. The layers were allowed to separate overnight. The aqueous layer was removed and the organic layer was washed with brine (1×5 vol). The layers were separated and the organic layer was dried over anhydrous $MgSO_4$, filtered and then concentrated under reduced pressure to yield a colourless oil. The colourless oil solidified on standing to a hard white solid.

E) Stage 5: Preparation of tert-butyl S-(2-aminoethyl)-N-(tert-butoxycarbonyl)-L-homocysteinate.

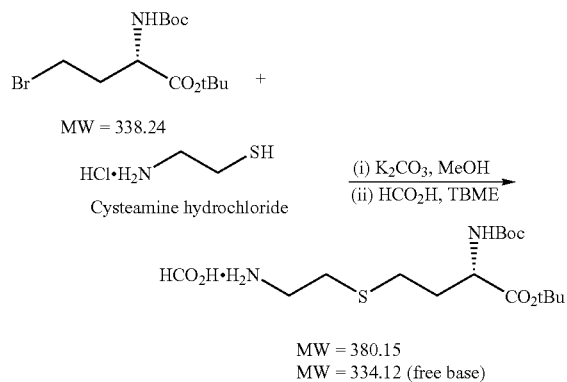

MW = 380.15
MW = 334.12 (free base)

The reaction was carried out under a nitrogen atmosphere. Anhydrous potassium carbonate (3.0 mol eq.) was added to a stirred suspension of cysteamine hydrochloride (1.5 mol eq.) in methanol (5 vol) at 20±3° C., under an atmosphere of $N_2$. The mixture was stirred for 30 minutes before a solution of tert-butyl (2S)-4-bromo-2-[(tert-butoxycarbonyl)amino] butanoate (1.0 mol eq., 1.0 wt) in methanol (5 vol) was added dropwise maintaining the contents temperature at 20±3° C. The reaction mixture was left stirring at 25±2° C. for 4 hours. The reaction mixture was concentrated under reduced pressure using a water bath at <30° C. to yield a white residue. The residue was partitioned between tert-butylmethyl ether (TBME; 8 vol) and water (8 vol). After 10 min. thorough shaking/mixing, the layers were allowed to separate. The aqueous phase was removed and the organic phase was concentrated under reduced pressure using a water bath at <30° C. to approximately half the volume (ca. 4 vol). Formic acid (1.0 mol eq.) was added, dropwise, to the stirred TBME solution maintaining a contents temperature of 20±3° C. The reaction mixture was stirred at 20±3° C. for one hour during which time a white precipitate formed. The mixture was cooled to 5±2° C. for at least 16 hours. The product was collected by filtration and then washed with additional TBME (2×1 vol). The solid was dried to constant weight in a vacuum oven at 40±2° C. affording the product as a white crystalline solid.

EXAMPLE 2

Alternative Preparation of Compound of Formula (II)

(2S)-2-Amino-4-bromobutanoic acid hydrobromide (1.0 wt, 1.0 mol) was suspended and stirred in tert-butyl acetate (TBA, 5 vols) at ca. 5° C. under a static nitrogen atmosphere. Concentrated sulphuric acid (98% purity; 1.2 mol eq.) was added to the suspension over 20 min, maintaining the contents temperature ~15° C. The contents were then warmed to around 20° C. and allowed to stir for at least 7 h at 20° C. After 1-2 h from the end of sulphuric acid addition, crystallisation was observed. 2M aqueous sodium hydroxide solution (8 mol eqs) was added over ca. 60 min maintaining the contents temperature ca. 20° C. The pH of the aqueous was checked and found to be above 9. The layers were separated and the aqueous layer discarded.

In a separate container, di-t-butyldicarbonate (99%; 0.95 mol eq.) was dissolved in TBME (2 vols). This solution was added, over 20 min, to the TBA solution, maintaining the contents temperature below 20° C. The solution was stirred at ca. 20° C. for 4 h.

32% w/w NaOH (4 vols) was charged to the reactor and cooled to ca. 10° C. Cysteamine hydrochloride (1.2 mol eq.) was added, maintaining the contents temperature at 10-20° C. This mixture was then stirred for ca. 30 min to allow for full neutralisation of the hydrochloride. The Aliquat 175 (methyl tributylammonium chloride; 75% w/w aqueous solution; 0.05 mol) was added maintaining the contents temperature at 10-20° C. The TBA/TBME solution was added to the aqueous over 20 min maintaining the temperature at ca. 20° C. The biphasic mixture was then stirred at ca. 20° C. for ca. 20 h. Water (4 vols) was then added over ca. 10 min maintaining the contents temperature at ca. 20° C. Stirring for 15 min gave 2 clear layers. The aqueous layer was separated and discarded. The organic layer is washed with water (2×4 vols). The organic solution was diluted by the addition of TBME (6-8 volumes). Formic acid (98% w/w; 0.8 mol eq) was then added, over 20 min, to the stirred TBA/TBME solution maintaining a contents temperature of ca. 20° C. The reaction mixture was cooled to −5° C. for 24 hours. The product was collected by filtration and then washed with additional TBME (2×1 vol). The solid was then dried in a vacuum oven at 40±5° C. affording the product as a white crystalline solid. The reaction scheme of this method is shown below:

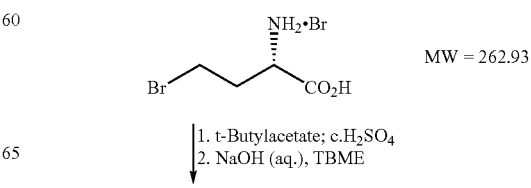

MW = 262.93

1. t-Butylacetate; c.$H_2SO_4$
2. NaOH (aq.), TBME

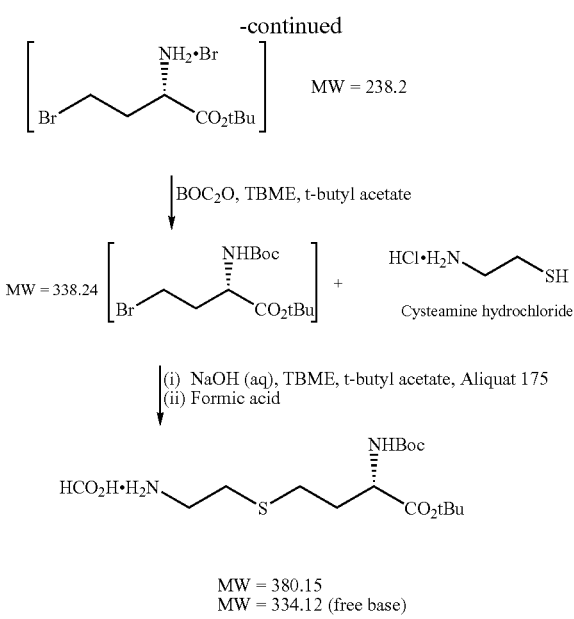

EXAMPLE 3

Preparation of Compound of Formula (III)

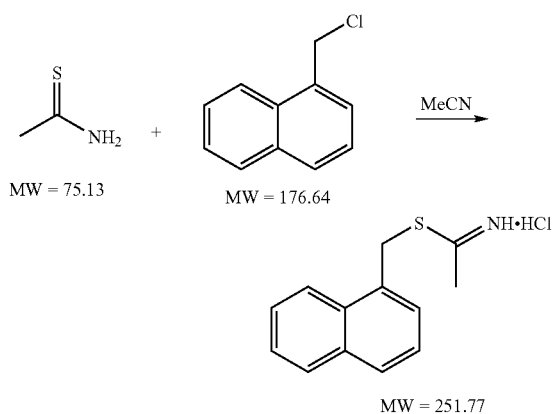

The reaction was carried out under a nitrogen atmosphere. Ethanethioamide (1 wt, 1 eq.) was added to acetonitrile (14 vol) with stirring under a nitrogen atmosphere. The resultant slurry was heated to 65° C. ±2° C. whereupon a yellow solution was formed. To this solution was added, dropwise, a separate solution of 1-(chloromethyl)naphthalene (2.47 wts, 1.05 eq.) in acetonitrile (3 vol), controlled in such a manner as to maintain the contents temperature at 60-650° C. Once the addition was complete, a further portion of acetonitrile (1 vol) was used as a line wash. The resultant solution was heated to 70° C. ±2° C.: crystallisation was observed within 10-20 minutes. The slurry was heated at 70° C. ±9° C. for a total of 3 hours and then cooled to room temperature. The solid was filtered, and the cake was washed with acetonitrile (2×5 vol). The resulting white solid was dried in vacuo at 45° C. ±50° C. for at least 16 hours.

EXAMPLE 4

Preparation of Compound of Formula (I) (Monohydrate)

The reaction was carried out under a nitrogen atmosphere. A mixture of tert-butyl S-(2-aminoethyl)-N-(tert-butoxycarbonyl)-L-homocysteinate compound with formic acid (1:1) (a compound of formula II) (1.0 mol eq, 1.0 wt) and 1-naphthylmethyl ethanimidothioate hydrochloride (a compound of formula III) (1.2 mol eq) was stirred in ethyl acetate (6 vol) at room temperature for 2 hours. Water (8.5 vol) was added and the mixture was vigorously stirred for 30 mins. The layers were allowed to settle and the aqueous layer containing tert-butyl N-(tert-butoxycarbonyl)-S-[2-(ethanimidoylamino)ethyl]-L-homocysteinate hydrochloride was collected. The aqueous layer was cooled to 0° C. and toluene (5 vol) was added. 32% w/w aqueous sodium hydroxide (2.5 mol eq) was slowly added, maintaining the temperature at 2° C. and the biphasic mixture was vigorously stirred for 10 min. The layers were separated, the aqueous layer was recharged to the vessel, and the toluene layer stored. Toluene (2.5 vol) was added to the aqueous layer and the mixture cooled to 0° C. 32% w/w aqueous sodium hydroxide (1.0 mol eq) was slowly added, maintaining the temperature at 0° C. and the biphasic mixture was vigorously stirred for 5 minutes. The layers were separated, the aqueous layer was discarded and the toluene layers containing tert-butyl N-(tert-butoxycarbonyl)-S-[2-(ethanimidoylamino)ethyl]-L-homocysteinate were combined in the vessel. An aqueous solution (2.5 vol) of orthophosphoric acid (1.5 mol eq) was added. The biphasic mixture was vigorously stirred at 70° C. for 12 hours. Water (4 vol) was then added and the mixture cooled to 40° C. The aqueous layer was separated and the pH was then adjusted to 5.5 using concentrated aqueous ammonia solution maintaining the temperature at 35° C. The resulting aqueous solution was heated to 75° C. and then ethanol (6.5 vol) added over 20 min. maintaining the temperature at 75° C. The solution was ramp cooled from 75° C. to 53° C. over 30 minutes and seeded. It was held at 53° C. for 2 hours and ramp cooled to 5° C. over 4 hours. The resulting slurry was held at that temperature for 20 hours. The product was collected by filtration and was washed with a 1:1 mixture of ethanol/water (2 vol) and then with ethanol (2 vol). A compound of formula (I), namely (2S)-2-amino-4-{[2-(ethanimidoylamino)ethyl]thio}butanoic acid, compound with phosphoric acid, monohydrate was dried at 60° C. in a vacuum to constant weight.

The reaction scheme of this method is shown below.

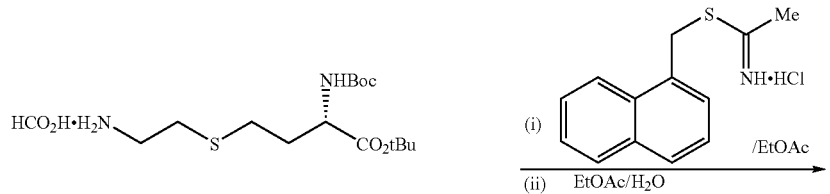

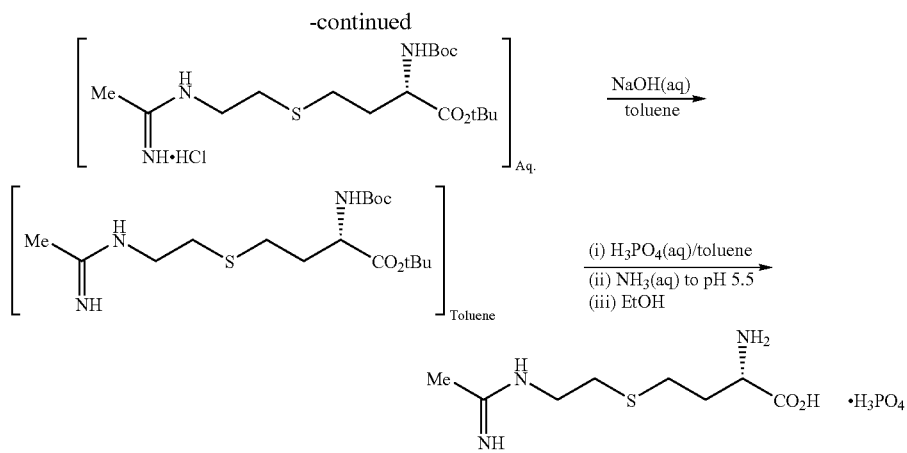

Figure 2:
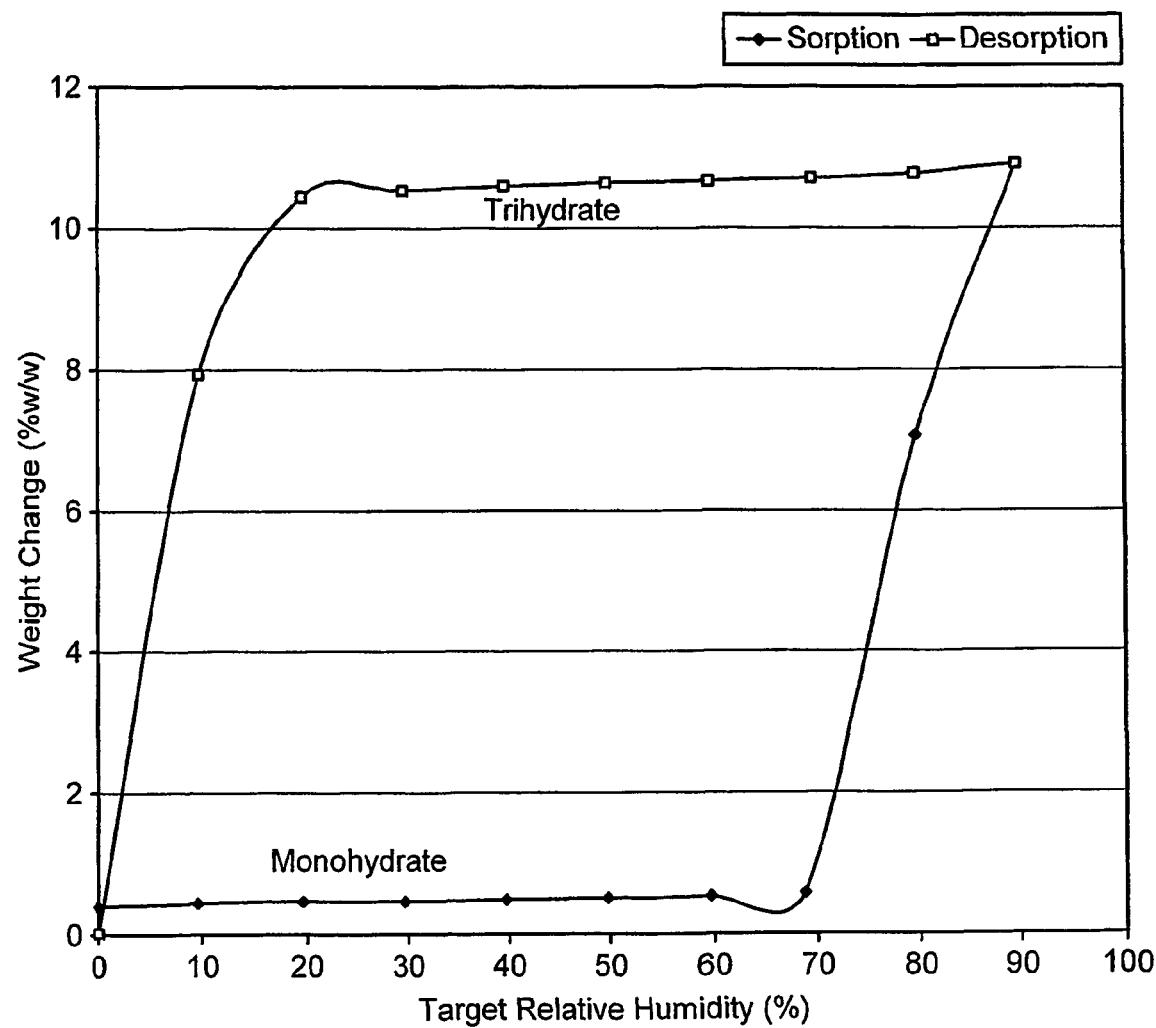
FIG. 2 is another full isotherm plot at 25 degrees C. of % target relative humidity against % weight change (w/w) showing moisture sorption and desorption for the compound of formula (I), monohydrate.
Figure 3:
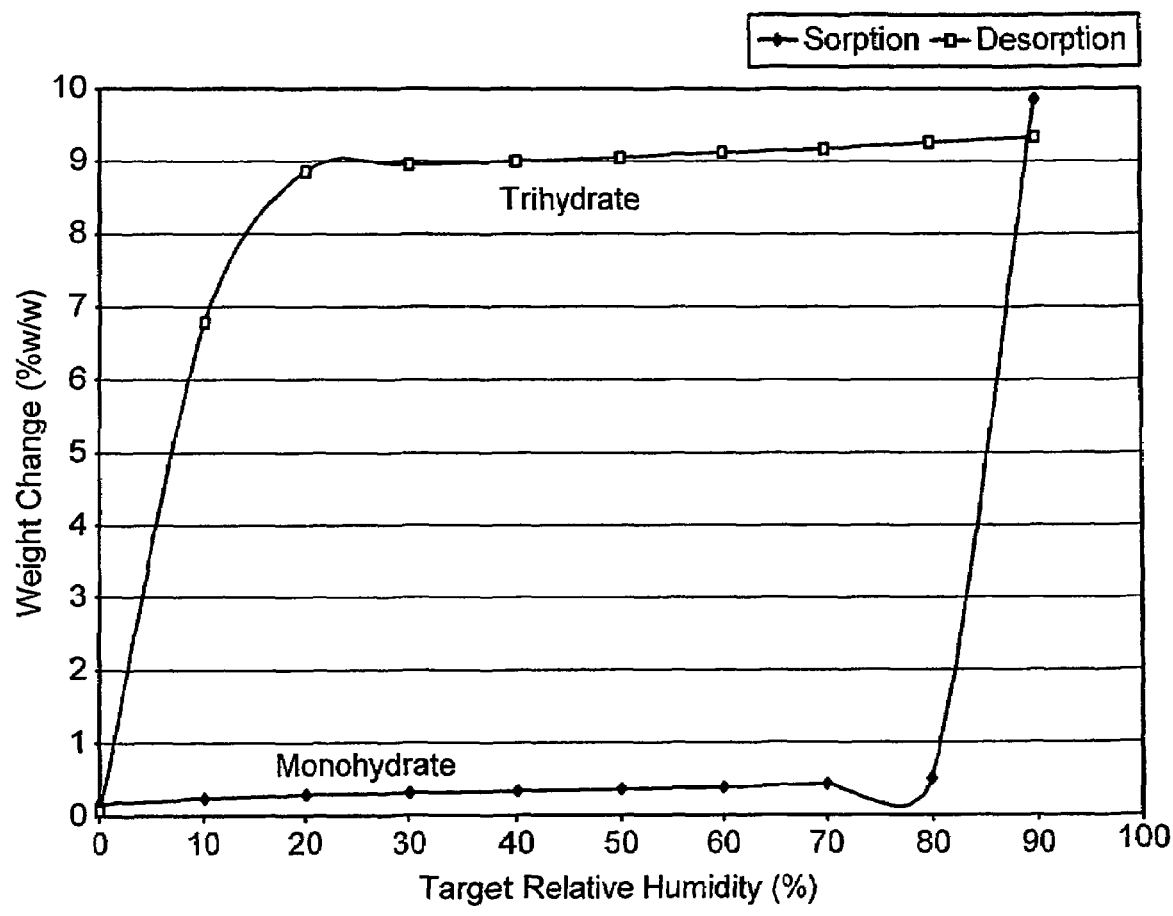
FIG. 3 is a further full isotherm plot at 25 degrees C. of % target relative humidity against % weight change (w/w) showing moisture sorption and desorption for the compound of formula (I), monohydrate.

The hygroscopicities of three samples of the compound of formula (I) monohydrate prepared in accordance with the above method were tested by measuring their % weight change (w/w) over a target relative humidity band of 0 to 90% at 25 degrees C. The results are shown in FIGS. 1 to 3.

To make these measurements, the following instruments and parameters were used:

Hiden IGASORP, Serial: IGA SA-040;
Hiden Intelligent Analyser, Model: HAS-022-120E, Serial: HALIGA-0042;
Flow=495 ml/min

| Isothermal Parameters: | |
| --- | --- |
| Analysis Mode: | F1 |
| Wait Until: | 97% |
| Min Time: | 10 minutes |
| Max Time: | 240 minutes |
| M-Level: | 0.2% |
| Isothermal sequence: | |
| Temperature: | 25° C. |

| Adsorption/% | Desorption/% |
| --- | --- |
| 0 | 80 |
| 10 | 70 |
| 20 | 60 |
| 30 | 50 |
| 40 | 40 |
| 50 | 30 |
| 60 | 20 |
| 70 | 10 |
| 80 | 0 |
| 90 | |

Scans=2 (1 cycle)

It can be seen from FIGS. 1 to 3 that there is no significant uptake of atmospheric moisture below a relative humidity of 70%.

Figure 6:
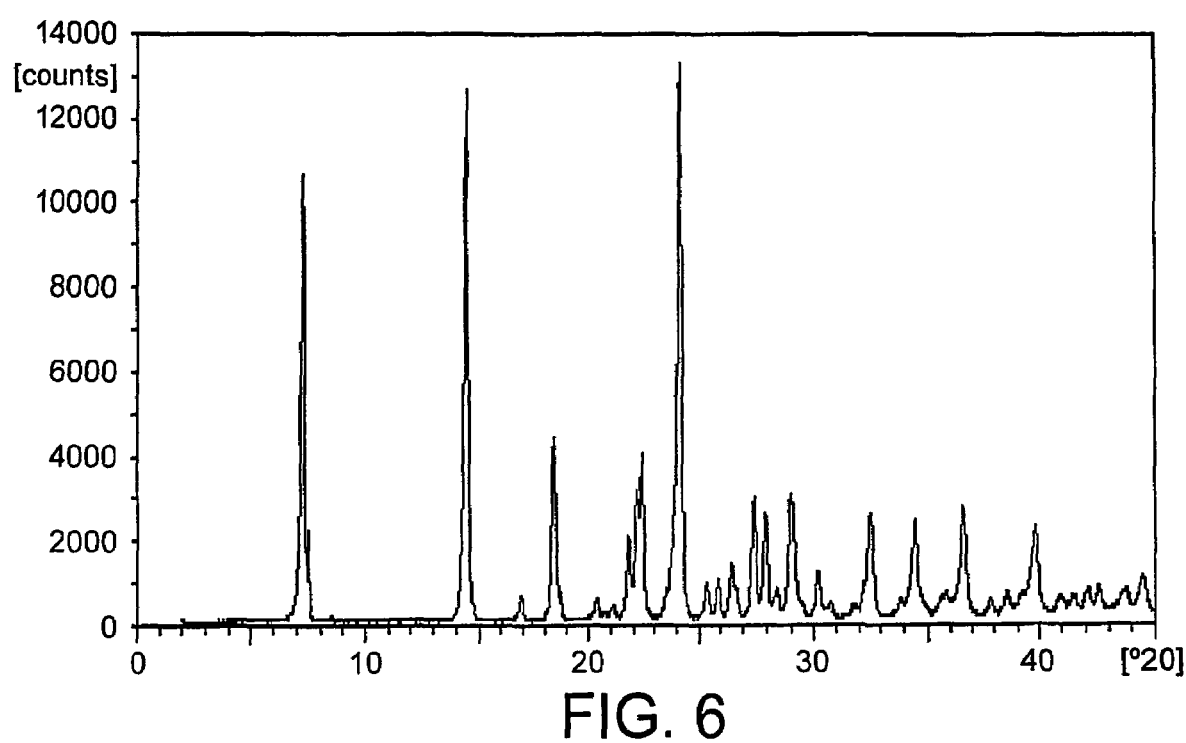
FIG. 6 is an X-ray diffraction pattern for a compound of formula (I) monohydrate.

X-ray diffraction data for (2S)-2-amino-4-{[2-(ethanimidoylamino)ethyl]thio}butanoic acid, compound with orthophosphoric acid, (1:1) hydrate is shown in FIG. 6. Table 1 below sets out the instrument and parameters used. Table 2 below sets out the peak listings.

TABLE 1

| Manufacturer | Philips Analytical X-Ray B. V. The Netherlands |
| --- | --- |
| Diffractometer Type | PW1800 (PC-APD) |
| Serial | DY701 |
| Tube Anode | Cu |
| LabdaAlpha1 | 1.54056 |
| LabdaAlpha2 | 1.54439 |
| RatioAlpha21 | 0.50000 |
| Divergence Slit | Automatic |
| Receiving Slit | Fine |
| Monochromator Used | YES |
| Generator Voltage | 40 |
| Tube Current | 45 |
| File Date & Time | 4-Oct-2000 3:23 |
| Data Angle Range (°2Θ) | 6.0000-45.0000 |
| Scan Step Size (°2Θ) | 0.020 |
| Scan Type | STEP |
| Scan Step Time | 4.00 |

TABLE 2

| Angle (°2Θ) | Relative Intensity (%) |
| --- | --- |
| 7.2900 | 100 |
| 7.5100 | 19.4 |
| 8.5000 | 1 |
| 12.0650 | 0 |
| 14.4950 | 60 |
| 16.9250 | 2 |
| 18.4300 | 16 |
| 18.6950 | 2 |
| 20.3350 | 2 |
| 20.7400 | 1 |
| 21.1200 | 1 |
| 21.8250 | 6 |
| 22.2150 | 10 |
| 22.4500 | 12 |
| 23.4950 | 2 |
| 23.7100 | 4 |
| 24.1450 | 38 |
| 25.3450 | 2 |
| 25.8800 | 2 |
| 26.4950 | 3 |
| 26.6750 | 2 |
| 27.4650 | 7 |
| 27.9600 | 6 |
| 28.4050 | 2 |
| 29.0200 | 7 |
| 29.4950 | 1 |
| 30.1800 | 3 |
| 30.7400 | 1 |
| 31.8000 | 1 |
| 32.1800 | 2 |

TABLE 2-continued

| Angle (°2Θ) | Relative Intensity (%) |
|---|---|
| 32.5200 | 5 |
| 33.8400 | 1 |
| 34.4650 | 5 |
| 35.5200 | 1 |
| 35.8150 | 1 |
| 36.5950 | 5 |
| 37.8300 | 1 |
| 38.5550 | 1 |
| 39.2200 | 1 |
| 39.7850 | 4 |
| 40.9400 | 1 |
| 41.5450 | 1 |
| 42.0900 | 1 |
| 42.5700 | 1 |
| 43.7200 | 1 |
| 44.4700 | 2 |

EXAMPLE 5

Preparation of Compound of Formula (I) (Trihydrate)

Compound of formula (I) monohydrate prepared according to the method of Example 4 (5 g) was exposed to a relative humidity of greater than 80% for 2 weeks. The product was analysed by X-ray powder diffraction and shown to be the trihydrate. (FIG. 7)

Figure 7:
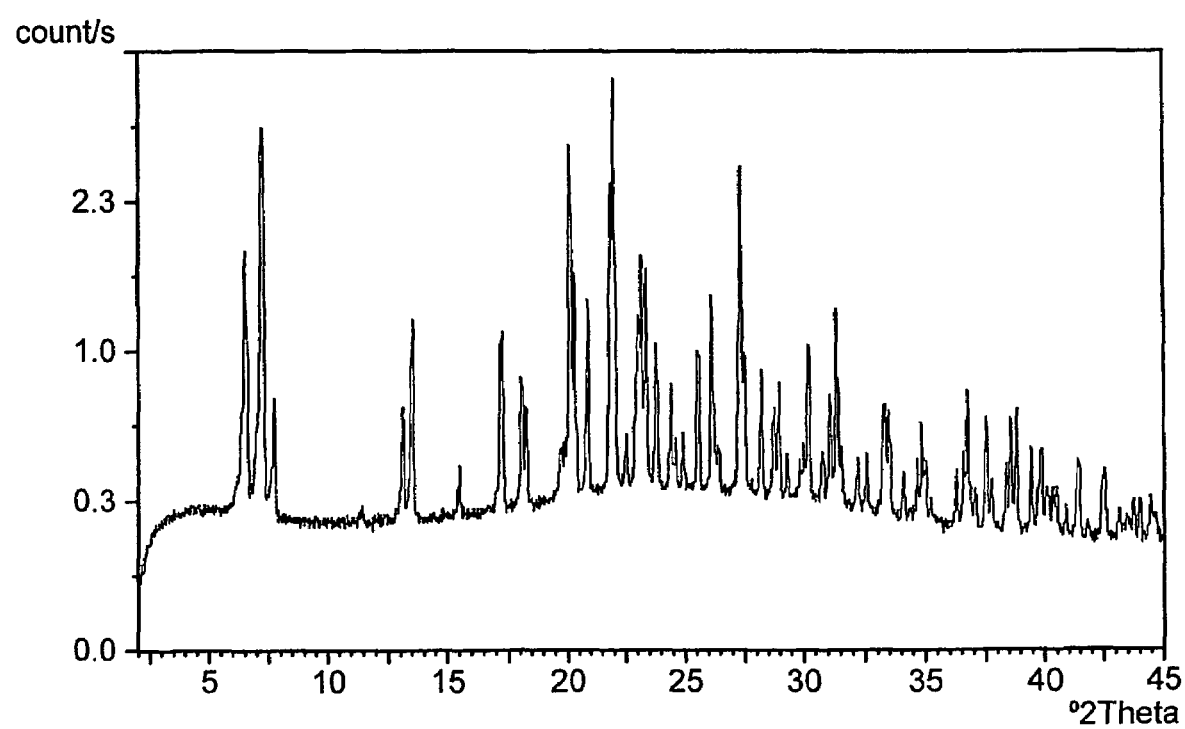
FIG. 7 is an X-ray diffraction pattern for a compound of formula (I) trihydrate

X-ray diffraction data for (2S)-2-amino-4-{[2-(ethanimidoylamino)ethyl]thio}butanoic acid, compound with orthophosphoric acid, (1:3) hydrate is shown in FIG. 7. Table 3 below sets out the instrument and parameters used. Table 4 below sets out the peak listings.

TABLE 3

| | |
|---|---|
| Manufacturer | Philips Analytical X-Ray B. V. The Netherlands |
| Diffractometer type | PW3040/60 |
| Serial Number | DY1379 |
| Tube Anode | Cu |
| K-Alpha 1 Wavelength (Å) | 1.54056 |
| Divergence Slit Angle (°) | 0.1250 |
| Receiving Slit | None |
| Monochromator used | YES |
| Generator Voltage | 40 |
| Tube Current | 45 |
| Data Angle Range (°2θ) | 5.000-45.000 |
| Scan Step Size (°2θ) | 0.0128 |
| Scan Type | Continuous |
| Scan Time per Step (s) | 2999.33 |
| Sample Preparation | Sample filled into a capillary tube |
| Detector | Raytech PSD |
| PSD mode | Scanning PSD |
| Number of active PSD channels | 591.00 |
| PSD pitch | 0.0533 |
| Divergence slit | Slit Fixed 1/8° |
| Hybrid Monochromator | 2xGe220 Asym. (hybrid) |
| Mirror | X-ray mirror Cu (hybrid MRD) |

TABLE 4

| Angle (°2θ) | Relative intensity (%) |
|---|---|
| 6.558 | 45 |
| 7.261 | 84 |
| 7.748 | 15 |
| 11.469 | 1 |
| 13.127 | 13 |
| 13.530 | 30 |
| 15.529 | 5 |
| 17.241 | 27 |
| 18.082 | 17 |
| 18.288 | 12 |
| 19.688 | 6 |
| 19.867 | 7 |
| 20.122 | 77 |
| 20.302 | 40 |
| 20.884 | 34 |
| 21.877 | 65 |
| 22.025 | 100 |
| 22.520 | 9 |
| 22.943 | 18 |
| 23.041 | 30 |
| 23.182 | 43 |
| 23.380 | 41 |
| 23.796 | 24 |
| 24.422 | 17 |
| 24.607 | 7 |
| 24.934 | 9 |
| 25.569 | 23 |
| 26.156 | 35 |
| 26.432 | 7 |
| 27.347 | 73 |
| 27.499 | 23 |
| 27.796 | 3 |
| 28.195 | 20 |
| 28.743 | 12 |
| 28.961 | 18 |
| 29.313 | 7 |
| 29.861 | 6 |
| 30.011 | 8 |
| 30.225 | 25 |
| 30.810 | 7 |
| 31.095 | 16 |
| 31.366 | 33 |
| 31.541 | 8 |
| 32.228 | 6 |
| 32.585 | 7 |
| 33.260 | 13 |
| 33.473 | 13 |
| 34.113 | 5 |
| 34.387 | 1 |
| 34.676 | 7 |
| 34.866 | 12 |
| 35.020 | 7 |
| 35.284 | 3 |
| 36.287 | 6 |
| 36.578 | 8 |
| 36.761 | 17 |
| 37.054 | 4 |
| 37.530 | 13 |
| 37.733 | 5 |
| 38.386 | 7 |
| 38.597 | 13 |
| 38.834 | 15 |
| 39.462 | 9 |
| 39.827 | 9 |
| 39.897 | 8 |
| 40.082 | 4 |
| 40.367 | 4 |
| 40.492 | 4 |
| 40.875 | 2 |
| 41.464 | 7 |
| 41.839 | 1 |
| 42.466 | 5 |
| 42.557 | 6 |
| 43.166 | 2 |
| 43.478 | 2 |
| 43.750 | 3 |
| 44.016 | 4 |
| 44.473 | 3 |
| 44.672 | 2 |

Figure 5:
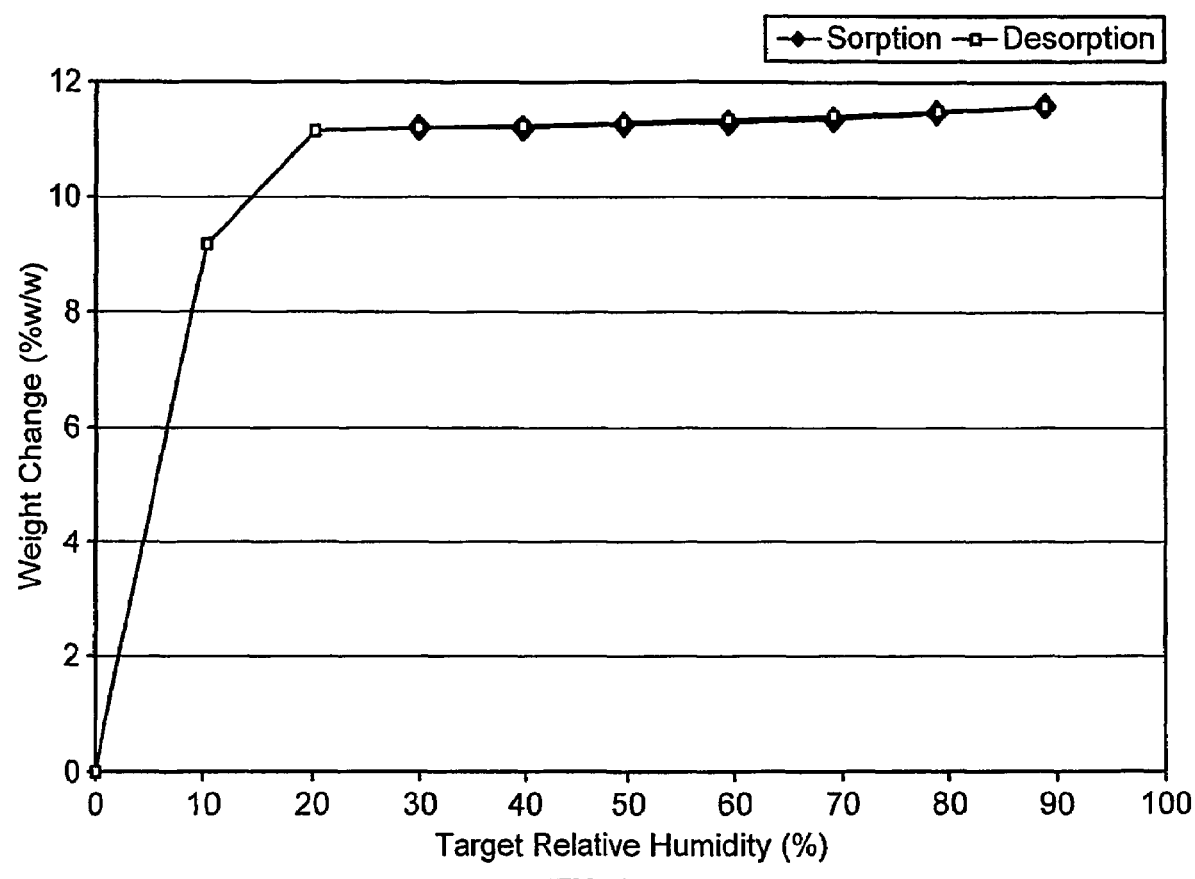
FIG. 5 is full isotherm plot a 25° C. of % target relative humidity against % weight change (w/w) showing moisture sorption and desorption for the compound of formula (I), trihydrate. The sorption and desorption traces are overlaid. The sorption isotherm started starts at a relative humidity of 30% increasing to 90%, followed by desorption from 90% RH to 0% RH.

The hydroscopicity of a sample of the compound of formula (I) trihydrate prepared in accordance with the above method was tested by measuring % weight change (w/w) over a target relative humidity band of 0 to 90% at 25° C. The instruments and parameters used were as for generation of the data shown in FIGS. 1 to 3. The results are shown in FIG. 5.

COMPARATIVE EXAMPLE A

A dihydrochloride salt of the compound of which the compound of formula (I) is the phosphate salt was prepared by reacting an intermediate product of example 1, namely tert-butyl N-(tert-butoxycarbonyl)-S-[2-(ethanimidoylamino)ethyl]-L-homocysteinate hydrochloride, with hydrogen chloride and dioxan at room temperature, as shown below.

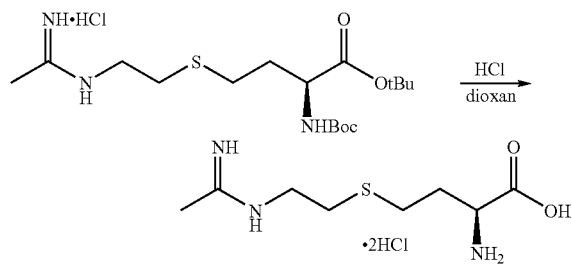

Figure 4:
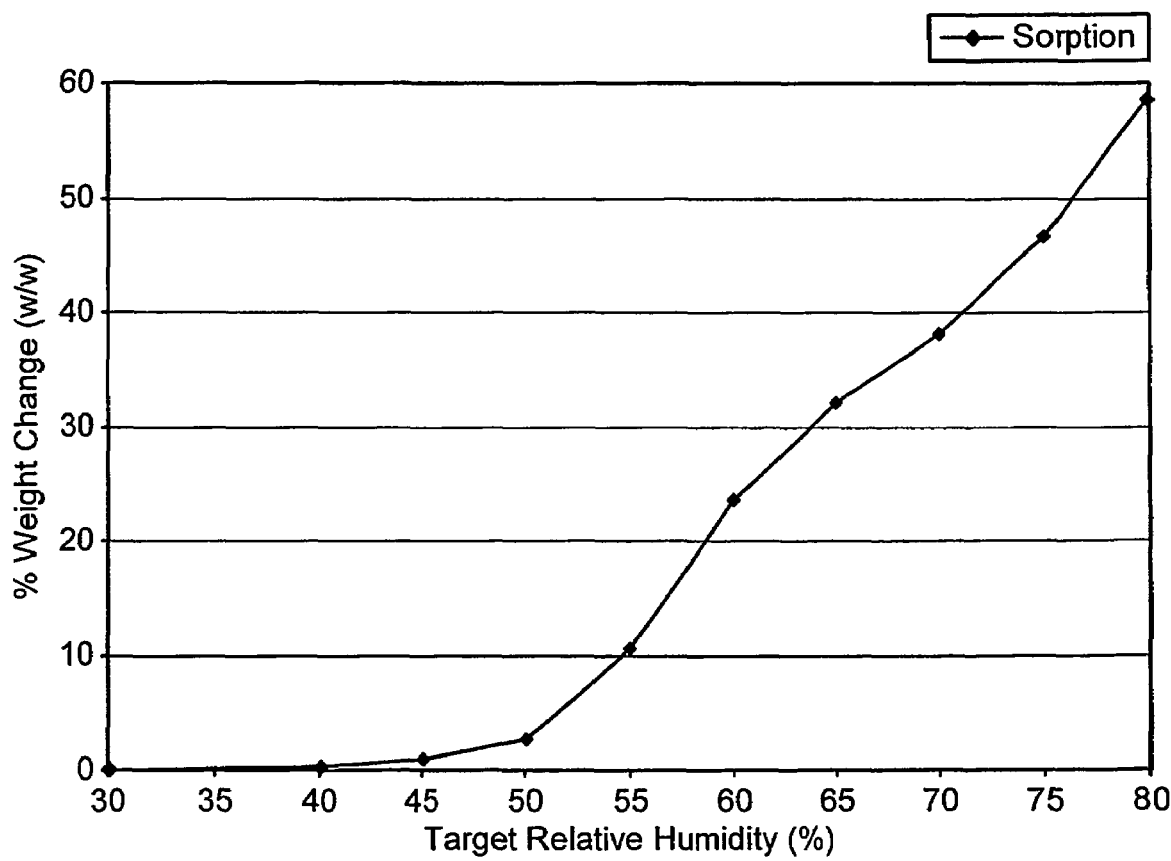
FIG. 4 is a comparative moisture sorption isotherm plot at 25 degrees C. of % target relative humidity against % weight change for (2S)-2-amino4-{[2-(ethanimidoylamino)ethyl]thio}butanoic acid, compound with hydrochloric acid.

The hygroscopicity of a sample of the dihydrochloride salt prepared in accordance with the above method was tested by measuring its % weight change (w/w) over a target relative humidity band of 30 to 80% at 25 degrees C. The results are shown in FIG. 4.

It can be seen that there was a rapid uptake of atmospheric moisture above 50% relative humidity. At 55% relative humidity, the dihydrochloride salt had a mass change of about 11%; at 60% relative humidity, the dihydrochloride salt had a mass change of about 24%; and at 65% relative humidity, the dihydrochloride salt had a mass change of about 32%. The mass change over a relative humidity range of 30-75% was about 47%.

The invention claimed is:

1. A compound of formula (I) being

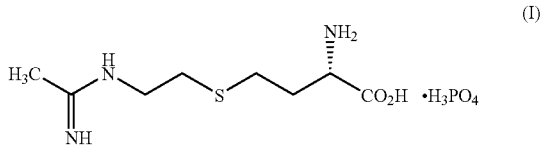

in the form of a hydrate, wherein said compound is selected from the group consisting of (i) (2S)-2-amino-4-{[2-(ethanimidoylamino)ethyl]thio}butanoic acid, (1:1) compound with orthophosphoric acid in the monohydrate form and (ii) (2S)-2-amino-4-{[2-(ethanimidoylamino)ethyl]thio}butanoic acid, (1:1) compound with orthophosphoric acid in the trihydrate form, which compound of formula (I) does not deliquesce below a relative humidity of 60% at 25 degrees C.

2. A method for the treatment of a clinical condition in a mammal for which an inhibitor of nitric oxide synthase is indicated, which comprises administration of a therapeutically effective amount of a compound as claimed in claim 1, wherein said clinical condition is selected from the group consisting of arthritis, ileus, migraine, pain and irritable bowel syndrome.

3. The method according to claim 2 wherein said mammal is a human.

4. The method according to claim 2 wherein the clinical condition is selected from the group consisting of arthritis and migraine.

5. A pharmaceutical formulation comprising a compound as claimed in claim 1 and a pharmaceutically acceptable carrier or excipient, and optionally one or more other therapeutic ingredients.

6. The pharmaceutical formulation as claimed in claim 5 which is a solid dosage form.

7. A process for preparing a compound as defined in claim 1 which comprises the following steps:
(i) reaction of the compound of formula (II)

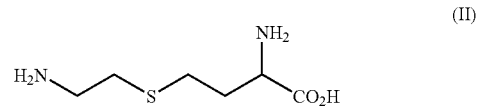

or an enantiomer, a salt, or a protected derivative thereof, with a compound of formula (III)

or a salt thereof, wherein L is a leaving group;
followed by the following steps in any order:
(ii) converting the resulting compound to a monophosphate salt;
(iii) removal of any protecting groups;
(iv) optional separation of an enantiomer from a mixture of enantiomers;
(v) conversion of the product to a corresponding hydrate.

8. The process as claimed in claim 7, wherein the step of converting the resulting compound to a monophosphate salt comprises a biphasic reaction using toluene and aqueous phosphoric acid.

9. The process as claimed in claim 7, wherein, following step (i): toluene is added to an aqueous layer resulting from the reaction of a compound of formula (II) or an enantiomer, a salt, or a protected derivative thereof with a compound of formula (III) or a salt thereof to form a biphasic mixture; a toluene layer is separated from this mixture; an aqueous solution of phosphoric acid is added to the toluene layer to form a further biphasic mixture; and an aqueous layer is separated from this further mixture.

* * * * *